US00PP19994P2

(12) United States Plant Patent
Ellefson

(10) Patent No.: US PP19,994 P2
(45) Date of Patent: May 12, 2009

(54) ***PIERIS* PLANT NAMED 'FIRE N ICE'**

(50) Latin Name: *Pieris ×japonica*
Varietal Denomination: FIRE N ICE

(76) Inventor: Jim Ellefson, P.O. Box 930, Mt. Angel, OR (US) 97362

( * ) Notice: Subject to any disclaimer, the term of this patent is extended or adjusted under 35 U.S.C. 154(b) by 10 days.

(21) Appl. No.: 11/982,074

(22) Filed: Nov. 2, 2007

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

Anonymous New Release from Kraemer's nursery available at: http://www.kraemersnursery.com/hot_list/Fire–n–Ice%20Flyer.pdf.*

* cited by examiner

*Primary Examiner*—Wendy C. Haas

(57) ABSTRACT

A new cultivar of *Pieris* named 'FIRE N ICE' that is distinguishable by upright bushy habit, clean bright, variegated foliage, fiery-red new growth, and cream-white flowers. In combination these traits set 'FIRE N ICE' apart from all other existing varieties of *Pieris* known to the inventor.

2 Drawing Sheets

Genus: *Pieris.*
Species: *×japonica.*
Denomination: 'FIRE N ICE'.

BACKGROUND OF THE INVENTION

The present invention relates to a new and distinct cultivar of *Pieris,* an evergreen shrub from the family Ericaceae. The new *Pieris* variety is grown as a specimen for woodland gardens, shrub borders and large containers. Known botanically as *Pieris×japonica* the new variety will be referred to hereinafter by the cultivar name 'FIRE N ICE'.

'FIRE N ICE' was discovered in a cultivated area of Mt. Angel, Oreg. The inventor selected 'FIRE N ICE' in 1992 as a naturally occurring branch sport of *Pieris japonica× formosa* var. *forestii* 'Forest Flame' (unpatented). Selection of 'FIRE N ICE' was based on the criteria of habit, vigorous growth, and clean bright variegated foliage that is medium-dark green with cream-white margins.

'FIRE N ICE' is distinguishable from 'Forest Flame' by variegated foliage. 'Forest Flame' does not exhibit any variegation. The two closest comparison plants are *Pieris* 'Variegata' (unpatented) and *Pieris* 'Flaming Silver' (unpatented). The new *Pieris* cultivar named 'FIRE N ICE' is distinguishable from the comparison plants by clean bright leaf variegation. In addition, 'FIRE N ICE' is distinguishable from *Pieris* 'Variegata' by improved habit and vigor.

'FIRE N ICE' is evergreen and is grown as a shrub or small tree, exhibiting upright bushy habit, vigorous growth, clusters of cream-white flowers, and variegated medium-dark green leaves with cream-white margins. The new leaf growth of 'FIRE N ICE' is fiery-red in color. At maturity 'FIRE N ICE' reaches 180 cm to 300 cm in height and 90 cm to 150 cm. in width. Cultural requirements are moisture retentive well-draining soil that is lime-free and humus-rich, sheltered location in dappled shade or full sun, and moderate water.

The first asexual reproduction of 'FIRE N ICE' was conducted in 1993 by the inventor in Mt. Angel, Oreg. The method used was semi-hardwood cuttings. Since that time under careful observation 'FIRE N ICE' has been determined uniform, stable and is true to type in subsequent generations of asexual propagation.

SUMMARY OF THE INVENTION

The following traits have been repeatedly observed and represent the distinguishing characteristics of the new *Pieris* cultivar named 'FIRE N ICE'. These traits in combination distinguish 'FIRE N ICE' from all other existing varieties of *Pieris* known to the inventor. 'FIRE N ICE' has not been tested under all possible conditions and phenotypic differences may be observed with variations in environmental, climatic, and cultural conditions, however, without any variance in genotype.

1. 'FIRE N ICE' exhibits upright bushy habit.
2. 'FIRE N ICE' exhibits cream-white flowers in spring.
3. 'FIRE N ICE' exhibits variegated medium-dark green foliage with cream-white margins.
4. 'FIRE N ICE' exhibits fiery-red new leaf growth.
5. 'FIRE N ICE' reaches 180 cm—300 cm in height and 90 cm–150 cm in width at maturity.
6. 'FIRE N ICE' is asexually propagated using the method of semi-hardwood cuttings.
7. 'FIRE N ICE' is hardy in USDA Zones 5–7.
8. 'FIRE N ICE' is an evergreen shrub or small tree.
9. 'FIRE N ICE' requires moisture retentive well-draining soil that is lime free and humus rich, sheltered location in full sun or dappled shade, and moderate water.

BRIEF DESCRIPTION OF THE DRAWINGS

The accompanying drawings illustrate the overall appearance of the new *Pieris* cultivar 'FIRE N ICE' showing color as true as it is reasonably possible to obtain in color reproductions of this type. Color in the drawings may differ from color values cited in the detailed botanical description, which accurately describe the actual color of the new variety 'FIRE N ICE'.

The drawing labeled

The drawing labeled

Figure 1:
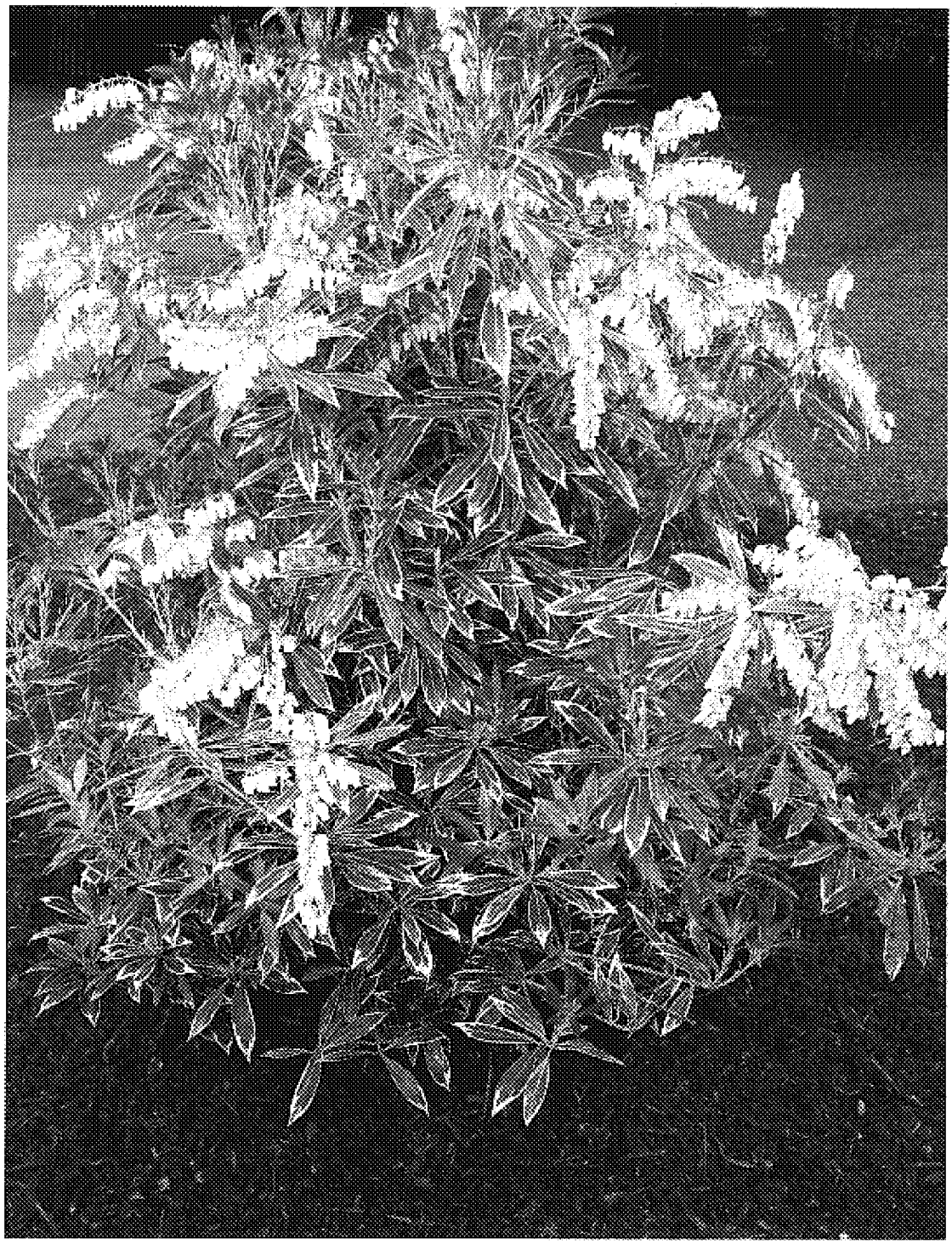
FIG. 1 depicts a 3 year old plant of 'FIRE N ICE'. The illustrated plant has been grown out of doors in Mt. Angel, Oreg. and is planted in a 3 gallon container.
Figure 2:
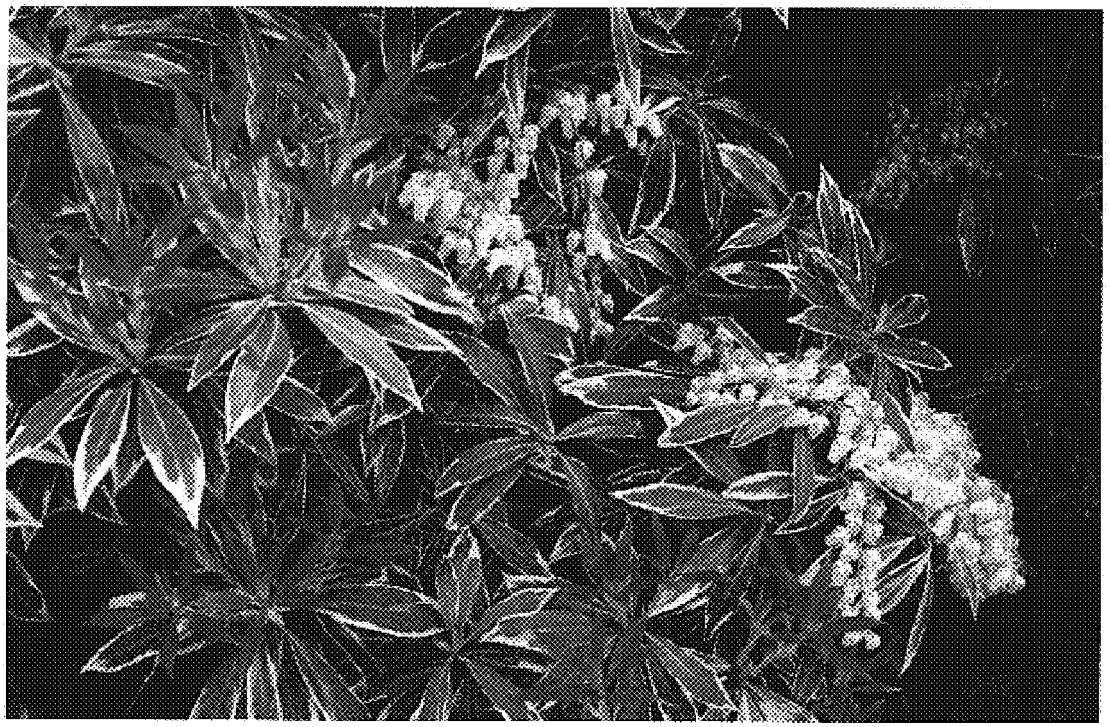
FIG. 2 depicts the spring appearance of 'FIRE N ICE' with its young red foliage, the cream-white margins of the mature leaf, and the inflorescence.

Drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Pieris* cultivar named 'FIRE N ICE'. Observations, measurements, values and comparisons were compiled in Arroyo Grande, Calif. from 18-month-old plants grown outdoors in 1-litre containers. Color determinations are made in accordance with the 2001 Royal Horticultural Society Colour Chart from London, England except where general color terms of ordinary dictionary significance are used. Growing conditions are similar to other *Pieris*.

Botanical classification: *Pieris×japonica* 'FIRE N ICE'.
Family: Ericaceae.
Genus: *Pieris*.
Species: *×japonica*.
Denomination: 'FIRE N ICE'.
Common name: Lily-of-the-valley.
Parentage: *Pieris×japonica* 'FIRE N ICE' was discovered as a branch sport of *Pieris×japonica* 'Forest Flame' (unpatented).
Propagation method: Semi-hardwood cuttings.
Rooting habit: Fine and fibrous.
Time to develop roots: 12–18 weeks are needed for the initial cuttings to develop roots.
Temperature to develop roots (range): 15–20° Centigrade air temperature.
Crop time (range): 12–15 months to produce a finished 1-litre container plant from a rooted cutting.
Habit: Upright bushy habit.
Vigor: Vigorous.
Suggested commercial container size: 1-litre commercial container.
Use: Specimen for woodland garden, shrub bordes, or large container.
Commercial category: Shrub or small tree.
Seasonal Interest: Spring flowers and fiery-red new leaf growth.
Inflorescence quantity (average): 40 per 1-litre container plant.
Flower quantity (average): 25 per inflorescence.
Dimensions first year (range): 40 cm–46 cm in height and width.
Dimensions at maturity (range): 180cm –300 cm in height and 90 cm –150 cm in width.
Cultural requirements: Moisture retentive well-draining soil that is lime-free and humus-rich, a sheltered location in dappled shade or full sun, and moderate water.
Disease: Fungal conditions common to other *Pieris*.
Pests: No susceptibility or resistance known to the inventor.
Hardiness: USDA Zones 5–7.

Stem:
*Branching habit.*—Divergent.
*Trunk dimensions* (*1-litre container plant*).—1.25 cm in width and 8 cm. in height.
*Trunk color.*—200D.
*Trunk surface.*—Scurfy.
*Stem color.*—183A and 138B.
*Stem shape.*—Terete.
*Stem surface.*—Glabrous.
*Stem strength.*—Strong.
*Stem length* (*average*).—15 cm.
*Stem diameter* (*average*).—0.25 cm.
*Internode length* (*range*).—0.25 cm. to 3.50 cm.

Foliage:
*Type.*—Evergreen.
*Arrangement.*—Alternate.
*Division.*—Simple.
*Shape.*—Oblanceolate.
*Leaf length.*—Ranges from 4 cm. to 6.50 cm.
*Leaf width.*—Ranges from 0.75 cm. to 1.75 cm.
*Leaf color* (*adaxial surface*).—137A, except margin and apex 161D.
*Leaf color* (*abaxial surface*).—138A, except margin and apex 161D.
*New leaf growth* (*abaxial and adaxial surfaces*).—45C.
*Apex.*—Acute.
*Base.*—Attenuate.
*Venation* (*adaxial surface*).—Prominent mid-vein.
*Venation* (*abaxial surface*).—Reticulate.
*Vein color.*—161D.
*Margin.*—Minutely crenate.
*Leaf surfaces* (*adaxial and abaxial*).—Glabrous.
*Attachment.*—Petiolate.
*Petiole length* (*average*).—6 mm.
*Petiole width* (*average*).—2 mm.
*Petiole color.*—181A.
*Petiole surface.*—Puberulent.
*Petiole shape.*—Sulcate.
*Stipules or spines.*—None observed.

Flower:
*Inflorescence.*—Panicle.
*Inflorescence quantity* (*average*).—20 panicles per 1-litre container plant.
*Inflorescence dimensions* (*average*).—17 cm. in length and 4 cm. in width.
*Inflorescence aspect.*—Pendulous.
*Bloom season.*—Spring.
*Peduncle length* (*average*).—6 cm.
*Peduncle shape.*—Terete.
*Peduncle color.*—181A.
*Peduncle surface.*—Stipitate glandular.
*Gland color.*—181A.
*Peduncle strength.*—Moderate.
*Pedicel dimensions.*—5 mm. in length and 0.50 mm. in diameter.
*Pedicel color.*—181A.
*Pedicel surface.*—Stipitate glandular.
*Gland colour.*—181A.
*Pedicel shape.*—Terete.
*Flower shape.*—Urceolate.
*Flower dimensions.*—1 cm. in length and 0.60 cm. in depth.
*Flower quantity* (*range*).—16–25 per inflorescence.
*Flower lastingness* (*average*).—2 weeks.
*Self-cleaning or persistent.*—Self-cleaning.
*Petal quantity.*—5 in number.

*Petals fused or unfused.*—Petals fused.
*Petal surface* (*ventral and dorsal surfaces*).—Glabrous.
*Petal margins.*—Entire.
*Petal apex.*—Rounded.
*Petal base.*—Truncate.
*Petal color* (*ventral and dorsal surfaces*).—155B.
*Calyx shape.*—Stellate.
*Calyx dimensions.*—6 mm. in diameter and 6 mm. in length.
*Sepal quantity.*—5 in number.
*Sepals fused or unfused.*—Sepals unfused.
*Sepal shape.*—Lanceolate.
*Sepal margin.*—Entire.
*Sepal apex.*—Acute.
*Sepal base.*—Truncate.
*Sepal dimensions.*—6 mm. in length and 2 mm. in width.
*Sepal surface.*—Stipitate glandular.
*Gland color.*—181A.
*Sepal color* (*adaxial and abaxial surfaces*).—161D and 181A and 191A all individually present.
*Flower fragrance.*—Moderately sweet scent.
*Bud shape.*—Ovate.
*Bud quantity* (*range*).—16–24 per inflorescence.
*Bud dimensions.*—4 mm. in length and 3 mm. in diameter.
*Bud surface.*—Stipitate glandular.
*Gland color.*—183A.
*Bud apex.*—Acute.
*Bud base.*—Rounded.
*Bud color.*—162B.

Reproductive organs:
*Stamen number.*—10 in number.
*Stamen color.*—138D.
*Stamen length.*—5 mm.
*Anther color.*—175A.
*Pollen quantity.*—Moderate.
*Pollen color.*—167A.
*Pistil.*—One.
*Pistil length.*—8 mm.
*Pistil shape.*—Pillar.
*Pistil color.*—138D.
*Stigma shape.*—Truncate.
*Stigma color.*—138D.
*Ovary position.*—Superior.
*Ovary dimensions.*—3 mm. in height and 3 mm. in diameter.
*Ovary shape.*—Subspherical.
*Ovary color.*—138C.

Seed: None observed to date.

It is claimed:

1. A new and distinct cultivar of *Pieris* plant named 'FIRE N ICE' as described and illustrated herein.

* * * * *